United States Patent [19]

Dvorak

[11] 4,205,672
[45] Jun. 3, 1980

[54] CONDUCTIVITY SENSING DEVICE FOR DIAPERS

[76] Inventor: Karel Dvorak, 345 Birchmount Rd., Scarborough, Toronto, Ontario M1N 3K1, Canada

[21] Appl. No.: 855,301

[22] Filed: Nov. 28, 1977

[51] Int. Cl.² .............. A61B 19/00; G08B 21/00; A61F 13/16
[52] U.S. Cl. .............. 128/138 A; 340/573; 340/604; 200/61.05; 128/287
[58] Field of Search ............ 128/138 A, 138 R, 2.12, 128/2.1 R, 417, 419 R, 734, 803; 340/573, 604; 200/61.05

[56] References Cited

U.S. PATENT DOCUMENTS

| | | | |
|---|---|---|---|
| 2,687,721 | 8/1954 | Ellison | 128/138 A |
| 3,460,123 | 10/1969 | Bass | 128/138 A |
| 3,508,235 | 4/1970 | Balsden | 128/138 A |
| 3,759,246 | 9/1973 | Flack | 128/138 A |
| 3,818,468 | 6/1974 | Toth et al. | 128/138 A |
| 4,014,323 | 3/1977 | Gilmer et al. | 128/2.12 |
| 4,069,817 | 1/1978 | Fendle et al. | 128/138 A |
| 4,106,001 | 8/1978 | Mahoney | 340/604 |

FOREIGN PATENT DOCUMENTS

| | | | |
|---|---|---|---|
| 807115 | 4/1951 | Fed. Rep. of Germany | 128/138 A |
| 1325775 | 3/1963 | France | 340/573 |

*Primary Examiner*—Robert W. Michell
*Assistant Examiner*—Arthur S. Rose

[57] ABSTRACT

A conductivity sensing device for diapers comprises a pair of swingably connected jaw members spring biased to closed position. One of the jaws has an electric conducting member with jaws designed to pierce material of the diaper to contact an electrically conducting layer therein. One of the jaws is provided with an electrical conducting area designed to contact the skin of a baby. Means are provided for preventing direct electrical contact between the jaws and the conducting area and means are provided to detect an increase in conductivity between these members.

2 Claims, 4 Drawing Figures

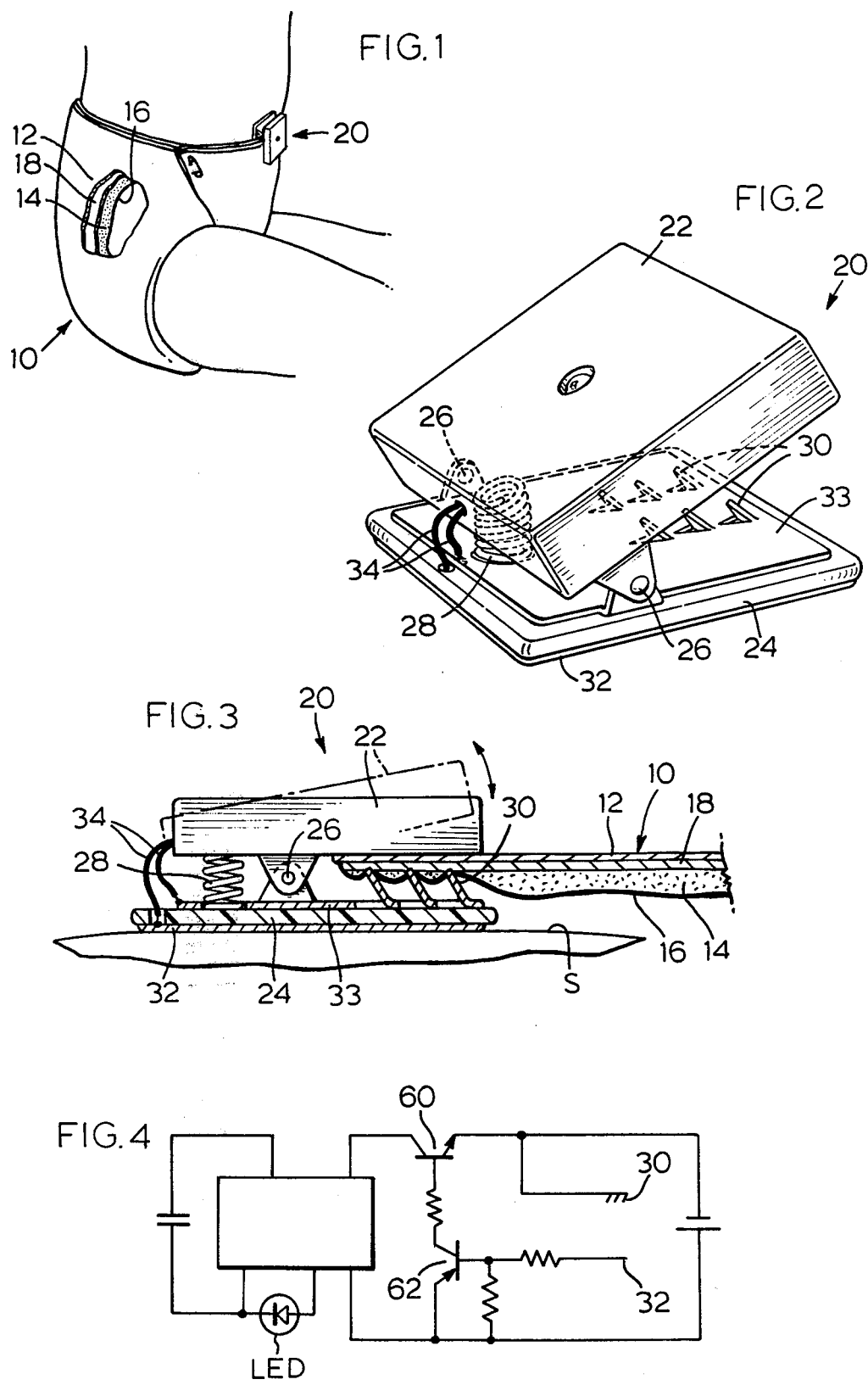

CONDUCTIVITY SENSING DEVICE FOR DIAPERS

This invention relates to a device for sensing dampness in a baby's diaper, a diaper for use therewith and the combination of such device and diaper.

Prior devices for sensing dampness in a diaper include: U.S. Pat. Nos. 3,460,123 by Bass; 2,687,721 by Ellison; 3,778,570 by Shuman; 3,696,357 by Kilogoro; 3,530,855 by Balding; 3,508,235 by Baisden; 2,907,841 by Campbell; 3,759,246 by Flack; 3,971,371 by Bloom; 3,809,078 by Mozes; 2,874,695 by Vaniman; French Pat. No. 1,368,844; Italian Pat. No. 615,866.

Such prior arrangements have the common feature that they describe a pair of conductive electrodes, built in some way into the diaper material. Manufacture of such diapers would be relatively expensive, which would inhibit and probably prohibit their use in the production of disposable diapers and for the consumer market.

With the inventive device herein disclosed, the diapers for use therewith may be easily manufactured without any retooling of the machinery existing for manufacture of the present diapers and with the necessity, only, of providing a single conducting area near one edge of the diaper which area extends into the part of the diaper extending between the infant's legs separated from the inner surface of the diaper by a conventional water permeable layer.

In accord with the invention there is provided a modified form of the conventional diaper and a device for sensing wetting by the baby. The diaper will include a conventional outer layer, conventionally of waterproof plastic, and an inner layer of urine absorbent material. The inner layer is commonly composed of a soft thick sub-layer and a stronger sub-layer which contacts the baby's skin retains the thick layer in place and allows the passage of moisture therethrough. In accord with the requirement of a sensing device in accord with the invention, there is provided a conducting area near the edge of the diaper and between the inner and outer layers.

The sensing device, in accord with the invention, (resembling in most embodiments a somewhat oversized cloths pin) comprises a pair of swingably connected jaw members biased toward closed position and designed to clamp in the close position on the edge of a disposable diaper. One jaw is provided with electrically conducting teeth which are designed to pierce a layer of the diaper and to contact the conducting area between the layers. One jaw (which may be the same as or different from as that bearing the teeth) is designed to reside between the inside of the diaper and the baby's body. The inwardly locatable jaw is provided with a conducting area for contacting the baby's body when the clip is in place on the diaper. Means are provided to prevent direct conduction between the teeth and the conducting area on the other arm. Electronic detection means are provided for detecting and signalling the change of conductivity between the piercing member on the one hand and the conducting area on the other. This conductivity is along a path from the teeth through the inner layer and along the baby's body to the conducting area (or vice versa) and the electronic detection means are designed to detect a change of conductivity along this path.

In drawings which illustrate a preferred embodiment of the invention:

FIG. 1 shows a broken away perspective of a diaper in accord with the invention;

FIG. 2 is a perspective of the device;

FIG. 3 shows a cross-section of the edge of such a diaper with the detection member applied thereto;

FIG. 4 shows a circuit which may suitably form the detector.

In the drawings FIG. 1 and FIG. 2 in cross-section show a disposable diaper 10 comprising a waterproof outer layer 12 of flexible plastic, and an inner layer comprising a thick porous, absorbent sub-layer 14 and a stronger water permeable sub-layer 16 is designed to be located inwardly of the sub-layer 14 and to retain sub-layer 14 in position. In addition to the conventional arrangement of layers 12, 14 and 16, conducting sub-layer 18 is provided between sub-layer 14 and inner layer 12 adjacent an edge of the diaper. The conducting sub-layer 18 of the diaper should extend into that part of the diaper extending between the infant's legs. The sub-layer 18 can be a piece of metal foil or can be made of metalized or treated cloth or paper. Alternatively a conducting coating may be placed, such as by painting, printing, straying or the like in one of the facing surfaces of layer 12 or of sub-layer 14. Although the conducting sub-layer 18 may, for manufacturing convenience and for convenience of use, extend over the whole diaper between layer 12 and sub-layer 14, there is only required a conducting sub-layer 18 extending to the intended crotch area from an edge of the diaper where the sensor device will be attached. For convenience this edge will preferably be one that will be an upper edge extending about the waist of the baby when the diaper is in use.

The sensing member 20, resembling in appearance a large clothes-pin comprises a pair of swingably connected jaws. In the preferred embodiment, a pair of plastic jaw members 22 and 24 are pivotably connected at pin 26 and biassed toward closed position by a compression spring 28. On jaw 24 electrically conducting teeth 30 on a plate 33 also of electrically conducting material are mounted so that when the sensing member is clamped on the edge of the baby's diaper, with the jaw member 24 inwardly thereof the teeth 30 will pierce sub-layers 14 and 16 and achieve electrical contact with sub-layer 18. An electrically conducting area 32 is located on the outside of member 24 arranged to contact the skin S of a baby when the sensing member is clamped to the edge of a diaper. Conducting area 32 and teeth 30 are, together, connected by electrical leads 34 to sensing means to be described. The conduction path between teeth 30 and sub-layer 18 is through the inner sub-layers 14 and 16 of the diaper and along the baby's skin (or vice verse). Means must be provided in the sensing member to ensure that the teeth 30 cannot directly contact area 32 or find a direct metal path thereto and short circuit the conduction path above-described. In the preferred embodiment this is performed by making the body of jaw 24, which separates teeth 30 and area 32, out of plastic. The teeth 30 may be directed perpendicular to plate 33. However, teeth 30 are preferably inclined toward the pivot point, as shown (i.e. inclined in a direction which will pierce the diaper material which the device is pulled away from the diaper). With the teeth thus inclined the device may first be clamped on a diaper and then pulled to ensure that the teeth pierce the diaper and reach the conducting sub-layer 18. This inclination of the teeth will also make it relatively difficult for the infant to detach the device from the diaper.

The preferred embodiment shows the teeth 30 on the same jaw member as the conducting area 32 contacting the baby's skin. The conducting area 32 is obviously always located on the inside surface of the jaw member, to be inwardly located on the diaper against the baby's skin. However the teeth may, if desired, be located on the outer jaw member 22 located to pierce the outer layer to reach the conducting area.

The resilient biasing means may be anything mechanically equivalent to the compression spring 28.

The sensing means may be any suitable electronic and indicating circuit preferably employing an integrated circuit for economy and ruggedness. A preferred form of such circuit is shown in FIG. 4.

In FIG. 4 the area 32 and teeth 30 are connected to the circuit as shown.

The circuit is designed so that the dry state of sub-layers 14 and 16 (and of the baby's skin) will prevent conduction in transistors 60 and 62. Wetting by the baby will increase the conductivity through sub-layers 14 and 16 and along the baby's skin sufficiently that the conductivity between area 32 and teeth 30 will increase sufficiently that transistor 62 and transistor 60 are turned on, applying battery power to the integrated circuit which is connected and designed on receipt of such signal to turn on the light emitting diode (LED). The circuit may and is customarily designed to cause the LED to blink. This light indicates that the diaper is wet.

The circuit shown may be replaced by any equivalent electric or electronic circuit of approximately equivalent compact, rugged and economic form with a suitable visual or audible signalling system.

I claim:

1. In combination:
    a diaper comprising an outer layer, a water permeable inner layer and,
    a conducting sub-layer between said layers, located adjacent an edge of the diaper, and extending into the part of the diaper which would extend between an infant's legs.
    a member having a pair of swingably connected jaws biased to closed position,
    said jaws being designed to be attached to said diaper such that one jaw is on one side and the other jaw is on the other side of the diaper,
    one of said jaws including a first electrically conducting member designed to pierce said inner layer when attached to said diaper and to contact said conducting sub-layer,
    said one of said jaws including a second electrical conducting member designed to contact the body of a baby when said one of said jaws is located on the inner side of said diaper,
    said one of said jaws further including means for electrically insulating said first conducting member from said second conducting member,
    and means for detecting and signalling an increase of conductivity between said first conducting member and said second conducting member.

2. A conductivity sensing device for diapers comprising:
    a member having a pair of swingably connected jaws spring biased to closed position,
    said jaws being designed to be attached to a diaper,
    such that one jaw is on one side and the other jaw is on the other side of a diaper,
    one of said jaws including a first electrically conducting member designed to pierce, the inner layer of a diaper, when attached to said diaper,
    said one of said jaws including an a second electrical conducting member designed to contact the body of a baby when said one of said jaws is located on the inner side of a diaper,
    said one of said jaws further including means for electrically insulating said first conducting member from said second conducting member,
    and means for detecting and signalling an increase of conductivity between said first conducting member and said second conducting member.

* * * * *